United States Patent
Nigon

(10) Patent No.: US 6,846,317 B1
(45) Date of Patent: Jan. 25, 2005

(54) KIT FOR REMOVING A BLOOD VESSEL FILTER

(75) Inventor: Alain Nigon, Bormes les Mimosas (FR)

(73) Assignee: ALN, Ghisonaccia (FR)

( * ) Notice: Subject to any disclaimer, the term of this patent is extended or adjusted under 35 U.S.C. 154(b) by 112 days.

(21) Appl. No.: 10/018,083

(22) PCT Filed: Jun. 13, 2000

(86) PCT No.: PCT/FR00/01624

§ 371 (c)(1),
(2), (4) Date: May 10, 2002

(87) PCT Pub. No.: WO00/76422

PCT Pub. Date: Dec. 21, 2000

(30) Foreign Application Priority Data

Jun. 14, 1999 (FR) .............................. 99 07690

(51) Int. Cl.[7] .............................................. A61M 29/00
(52) U.S. Cl. ...................................... 606/200; 606/114
(58) Field of Search ................................. 606/113, 114, 606/127, 191, 198, 205, 206, 200

(56) References Cited

U.S. PATENT DOCUMENTS

| | | | |
|---|---|---|---|
| 4,655,219 A | | 4/1987 | Petruzzi |
| 4,990,156 A | * | 2/1991 | Lefebvre ..................... 606/200 |
| 5,370,657 A | | 12/1994 | Irie |
| 5,512,037 A | | 4/1996 | Russell et al. |
| 5,700,269 A | | 12/1997 | Pinchuk et al. |
| 5,725,550 A | * | 3/1998 | Nadal ......................... 606/200 |

FOREIGN PATENT DOCUMENTS

| | | |
|---|---|---|
| EP | 0 813 842 A2 | 12/1997 |
| WO | WO 98/33443 A1 | 8/1998 |
| WO | WO 00/16845 A1 | 3/2000 |

* cited by examiner

*Primary Examiner*—Mike Milano
(74) *Attorney, Agent, or Firm*—Browdy and Neimark, P.L.L.C.

(57) ABSTRACT

A kit for the withdrawal of a blood vessel filter of the umbrella type formed from a bush (31) serving as a sleeve for retaining a number of flexible strands (32) that spread apart naturally and end in hooks (33) directed outwards so that they lock onto the wall of a vessel, comprising a first so-called "external" catheter (1)

a stem that can be inserted in the external catheter and has, at one of its ends, a number of flexible legs (18) that open out from the stem, spreading apart naturally and ending in hooks (20) directed inwards for grasping bush (31) of the filter as they close up again and preferably in addition a second catheter (11), of diameter such that it can be introduced into the external catheter (1).

11 Claims, 3 Drawing Sheets

KIT FOR REMOVING A BLOOD VESSEL FILTER

The present application is the national stage under 35 U.S.C. 371 of international application PCT/FR00/01624, filed which designated the United States, and which international application was not published under PCT Article 21(2) in the English language.

BACKGROUND OF THE INVENTION

1. Technical Field of the Invention

The present invention relates to a kit for the withdrawal of a filter for blood vessels.

Two main types of filters for the inferior vena cava are known at present. It should be recalled that a filter for the inferior vena cava is a device consisting of metallic strands resembling the frame of a half-open umbrella but having only the ribs and the bosshead of the latter, which is installed in the inferior vena cava. The metallic strands are provided with hooks at their free end, enabling them to cling to the vessel wall.

2. Prior Art

These metallic strands ore thin and flexible and they therefore beat in rhythm with the peristaltic movements of the inferior vena cava. These movements, which cause the metallic strands to come closer and move away alternately, make it possible, when the umbrella filter blocks a clot, for the latter to be sheared progressively into small pieces that can no longer be harmful.

The first type of filter is the permanent type; in this case an umbrella filter is installed above in the inferior vena cava, and is left there permanently. The medical profession is always reluctant to leave a foreign body in the human body permanently.

Temporary filters are also known. In this case a filter is fitted to the end of a catheter which is left in place and is withdrawn when the time comes. However, the catheter can cause adhesions, which tear the vessel wall on withdrawal. Furthermore, being about fifty centimeters long, the catheter must remain partially outside of the body, and so is a source of infection. That is why patients fitted with a temporary device are maintained under strict hygiene and receive permanent antibiotic-based medication.

OBJECTS AND SUMMARY OF THE INVENTION

It would therefore be desirable to be able to install, in the inferior vena cava and in other vessels, an umbrella filter of the permanent type, i.e. of the type where the metallic strands have a hook at their free end, but which can nevertheless be removed.

Now, after much research, the applicant discovered that a kit comprising a catheter and a stem ending in hooked flexible legs made it possible to grasp umbrella filters of the permanent type and compress their strands so as to unhook them from the vessel wall without damaging the latter.

Accordingly, the present application relates to a kit for the withdrawal of a blood vessel filter of the umbrella type formed from a bush serving as a retaining sleeve for a number of flexible strands that spread apart naturally and end in hooks directed outwards so that they lock onto the vessel wall, characterized in that it comprises a first, "external" catheter a stem that can be inserted in the external catheter and having at one of its ends a number of flexible legs which open out from the stem, spread apart naturally and ending in hooks directed inwards for gripping the bush of the filter as they close up.

It is thus possible to close up the legs mounted at the end of the stem, by pushing the stem, to insert them into the first catheter until they are near the end of the said first catheter, to advance the assembly until it is near the bush of the filter and to advance the stem to make the legs come out and thus allow them to open out. It then only remains to advance the first catheter in its turn so as to close the legs back onto the bush and thus grasp it, again advance the first catheter to close the filter strands again, taking them into the filter, then pull the stem for extracting the filter, possibly at the same time as the first catheter.

Although a device of this kind already proves satisfactory, in preferred conditions of application, the above kit is characterized in that it comprises, in addition, a second catheter, of a diameter such that it can be introduced into the external catheter.

Thus, the stem and its closed-up flexible legs can be installed in the said second catheter from the outset, making it unnecessary, in particular, for the legs mounted at the end of the stem to be closed up again at the time of use. The stem, pre-installed in the second catheter, can be packed separately with the latter in a second sterile pack.

Accordingly, the present application also relates to a kit as above, characterized in that the stem that can be inserted in the external catheter and that has a number of flexible legs at one of its ends, has a length that is greater than that of the second catheter and, before it is used for gripping the bush of the filter, it is installed in the second catheter in order to keep the said flexible strands of the stem closed up.

The introduction of a hollow catheter, even if chamfered, into blood vessels is not easy to execute without risk of injury.

Therefore the present application also relates to a kit as above, characterized in that it additionally comprises a third catheter, of suitable diameter for introduction into the external catheter, the leading end of which is closed and chamfered to serve as a dilator during introduction of the assembly, consisting of the first and the said third catheter, into a vessel.

To the extent that the third catheter is to serve as a dilator, it will be understood that its length is greater than that of the first catheter and therefore it will go past the end of the said first catheter during introduction into vessels. The outside diameter of the third catheter is preferably adjusted to the inside diameter of the first catheter as a sliding fit.

Polyethylene is preferably used as the material for making the catheters.

The stem and its hooked legs will preferably be made of stainless steel. Its handle, if it has one, could also be made of polyethylene for example.

The length of the catheters can range for example from 20 to 100 cm, preferably from 30 to 90 cm, especially from 40 to 80 cm, and quite particularly from 45 to 60 cm.

The inside diameter of the catheters can range for example from 4.7 mm to 2.3 mm, preferably from 4.3 to 2.7 mm, more particularly from 3.3 to 2.7 mm for the external catheter and for example from 4.0 mm to 1.67 mm, especially 3.3 mm to 2 mm, and in particular from 2.7 to 2 mm for the second catheter. In particular, a diameter 9F will be used for the first catheter and a diameter 7F for the second catheter. Note that diameters of 9F and 7F correspond to 3.0 and 2.3 mm respectively.

Under preferred conditions of application of the kit described above, the third catheter includes at least one device that can be detected from outside the body, located near its front end. Thus, it is possible to follow the progress of the assembly towards the filter.

The device detectable from outside the body could be, for example, a ring, especially radiopaque, fitted or inserted on or in a catheter, preferably of stainless steel, especially of gold, and quite particularly of platinum-iridium. It can also be a spot or dot, or the entire catheter could be radiopaque.

Under other preferred conditions of application of the kit described above, the device that is detectable from outside the body can be detected by the same detection device as that used for the bush of the filter. Thus, one and the same detector, for example using radioscopy, makes it possible to locate the filter and its bush in the body, and monitor the passage of the catheters towards them.

The kit according to the invention, in its most elaborate version employing, in addition to the stem, two hollow catheters and a dilator catheter, can be used as follows, in the case of an inferior vena cava:

The right jugular vein is punctured using a puncturing needle. A Teflon®-coated J-shaped guide is passed down with the aid of a stiffener until it is 5 cm above the filter to be extracted, following its progress by radioscopy. The puncturing needle is withdrawn. The assembly of the first and third catheters is made to slide along the J-shaped guide as far as its distal part, following its progress by radioscopy on account of a radiopaque ring. The J-shaped guide and the third catheter are withdrawn simultaneously under frontal and especially profile radioscopy. A wedge is fitted between the handle of the stem ending in hooked flexible legs and the entry point of the second catheter to prevent inadvertently pushing the stem back and opening the vulsella forceps like an umbrella. The second catheter, with the stem inside, is introduced, making sure that it does not go down beyond the reserved 5 cm and continuing to monitor the entire manipulation by radioscopy. Then the wedge is removed and the stem is advanced slightly to open the vulsella forceps. Once the recovery hooks are open, go down slowly to above the bush of the filter to be recovered. Make sure that the hooks are positioned sufficiently beneath the bush. At this point of the procedure, slowly slide the first catheter over the hooks at the end of the stem. Block by refitting the wedge or a wedge that is somewhat shorter, still under radioscopy, ensure that the hooks of the forceps are properly closed under the bush of the filter and are well centred. Continue to move the first catheter down slowly beyond the bush of the filter, so as to fold its strands inwards. Make sure that the hooks of the filter are properly unhooked from the vessel wall. With a slow withdrawing movement, withdraw the stem and the filter which it has gripped, making sure that the filter has been drawn into the second catheter completely. Bring out the assembly of the first and second catheter with the stem and the filter. Then provide haemostasis at the puncture point.

BRIEF DESCRIPTION OF THE DRAWINGS

The invention will be better understood by referring to the appended drawings, in which.

DETAILED DESCRIPTION OF THE PREFERRED EMBODIMENT(S) OF THE INVENTION

Figure 1:
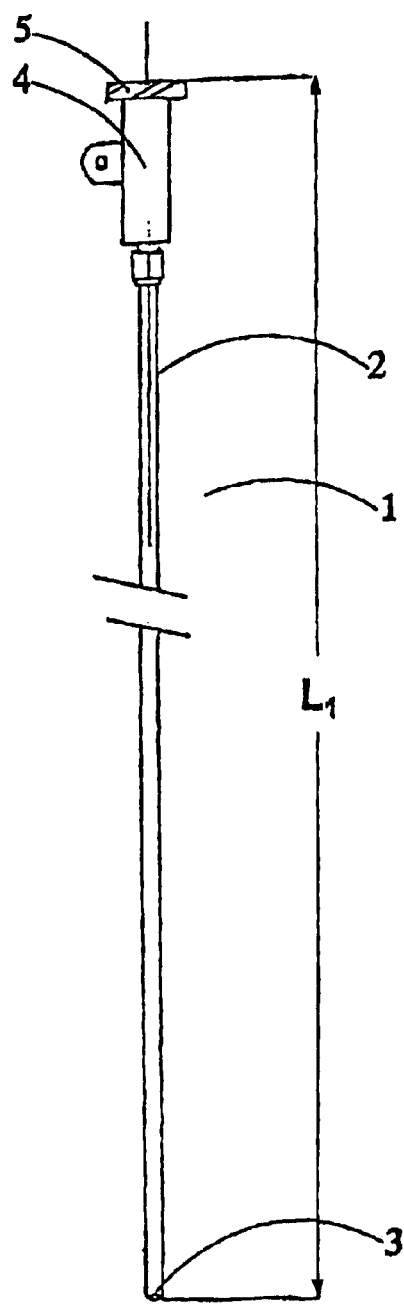
FIG. 1 shows a side view of a first, so-called "external" catheter according to the invention.

In FIG. 1 we can see a first catheter 1, called "external", consisting of a hollow tube 2 of polyethylene with inside diameter 9F (3.0 mm) provided with a chamfered front end 3. The rear end is provided with a wider part 4 to facilitate its manipulation, and ends in a flange 5. If desired, the front end 3 is provided with an annular radiopaque zone that can be detected from outside the body. Its length $L_1$ is 550 mm.

Figure 2:
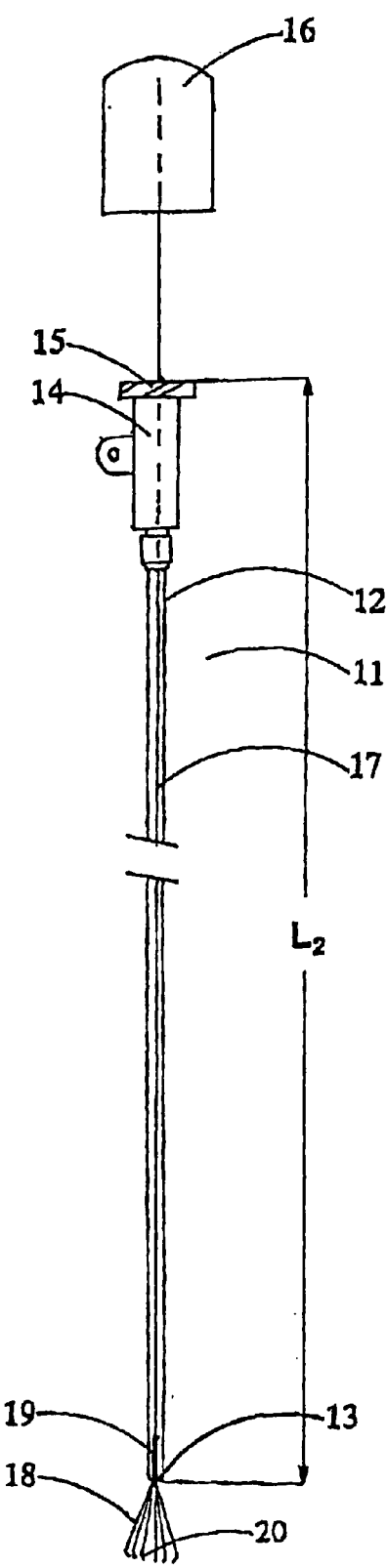
FIG. 2 shows a side view of a second catheter according to the invention with a stem positioned for grasping the bush of a filter.

FIG. 2 shows a second catheter 11. This second catheter has the same general configuration as the first catheter. Thus, it is provided with a chamfered front end 13. The rear end is provided with a wider part 14 ending in a flange 15. Its length $L_2$ is 553 mm and its inside diameter is 7F (2.3 mm) so that it can be inserted in the first catheter 1.

A stem is installed in position for grasping the bush of a filter. It has a manipulating handle 16 of polyethylene moulded on stem 17 proper, made of stainless steel. At the other end there is a number of flexible legs 18, also of stainless steel, secured to stem 17 by means of a sheath 19. These flexible legs 18 end in hooks 20 directed inwards for grasping the bush of the filter when they are closed up. They open out from stem 17, and they spread apart naturally if no force is applied to them. It will be understood that if the first catheter 1 is caused to advance towards the end of the stem, the legs 18 will be closed again, bringing the hooks 20 closer together. It is in this position with the legs closed up that the assembly of the second catheter 11 and the stem can be introduced into the first catheter 1.

Figure 3:
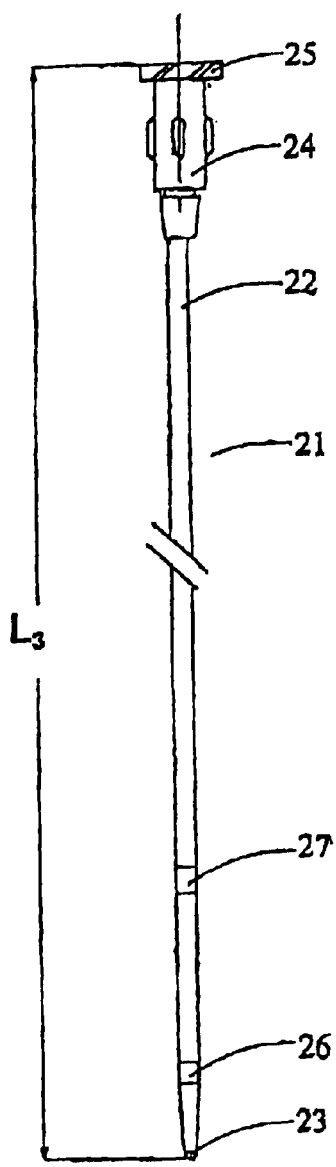
FIG. 3 shows a side view of a third catheter according to the invention that serves as a dilator.

In FIG. 3 we can see a third catheter 21 serving as a dilator. This third catheter 21 has to some extent the same general configuration as the first and second catheters. Thus, it has a rear end that is provided with a wider part 14 ending in a flange 25. Its front end 23 is chamfered but has a slightly conical shape and in particular it is closed. Its length $L_3$ is 605 mm and its inside diameter is 7F so that it can be inserted in the first catheter 1. This third catheter 21 is provided with two radiopaque annular zones that can be detected from outside the body using X-rays, one 26 near the chamfered front end and the other 27 at a distance of 560 mm from its rear end.

The third dilator catheter 21 is firstly installed in the first "external" catheter 1, the assembly is introduced into the vascular system as far as the filter, and secondly the third catheter 21, which is no longer of use, is replaced by the second catheter 11 containing the stem, grasping the filter and removing it, on withdrawing the stem, the second catheter 11 and the first catheter 1.

Figure 4:
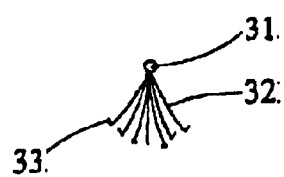
FIG. 4 shows a blood vessel filter of the umbrella type.

FIG. 4 shows a filter that can be removed from the vascular system by means of a kit according to the invention. It comprises a bush 31 serving as a retaining sleeve for a number of flexible strands 32 which spread apart naturally and end in hooks 33 directed outwards so that they lock against and in the wall of a vessel. The end of each strand constituting the hook 33 forms an angle from 91 to 95°, or even more, relative to the strand 32 so that it can be removed without causing damage. The rim formed by bush 31 among strands 32 enables it to be gripped by hooks 20 of the stem.

What is claimed is:

1. A kit for the withdrawal of a blood vessel filter, the filter having a bush (31) and a plurality of flexible strands (32) fixed to the bush (31) at a first end thereof, a second free end of the strands having hooks (33) directed outward so as to engage the inner wall of a blood vessel, the kit comprising:

a first external catheter (1) having a through hole along the longitudinal axis thereof;

a second catheter (11) having a through hole along the longitudinal axis thereof and a diameter allowing slidable engagement of the second catheter in and for the entire length of the through hole of the first external catheter (1), and a stem having a plurality of flexible legs (18) fixed at one end of the stem, the flexible legs (18) extending naturally outward from the one end of the stem, a free end of the flexible legs (18) having hooks (20) which extend inwards toward an extension of the longitudinal axis of the stem and can grasp the bush of the filter when compressed around the bush, wherein said stem can be slidably engaged in said second catheter (11) to compress the flexible legs (18) within the second catheter (11) or to release the flexible legs so as to be positioned over the bush, and wherein an assembly of the stem, second catheter, and first external catheter can be inserted within the blood vessel for removal of the filter after the flexible legs have been positioned the bush and then compressed by the second catheter to engage over the bush and the flexible strands of the filter have been compressed by the first external catheter.

2. A kit according to claim 1, wherein the stem has a length that is greater than that of the second catheter (11) and prior to use of the stem for grasping the bush (31) of the filter, is installed in a second catheter (11) so that the said flexible legs (18) of the stem are compressed within the second catheter.

3. A kit according to claim 1, wherein the kit comprises a third catheter (21), of a diameter suitable for introduction into the external catheter (1) when not engaged to the second catheter, the front end (23) of which is closed and chamfered for serving as a dilator during introduction of an assembly consisting of the first catheter (1) and the said third catheter (21) into the blood vessel.

4. A kit according to claim 3, wherein the third catheter (21) includes at least one device (26) that is detectable from outside the body, located near a front end of the third catheter.

5. A kit according to claim 4, wherein the one device (26) that is detectable from outside the body can be detected by the same detecting device as that used for detecting the bush (31) of the filter.

6. A kit according to claim 3, wherein the length of the first, second and third catheters ranges from 40 to 80 cm.

7. A kit according to claim 1, wherein the inside diameter of the first external catheter ranges from 4.7 mm to 2.3 mm and from 4.0 mm to 1.67 mm for the inside diameter of the second catheter.

8. A kit according to claim 4, wherein the device that is detectable from outside the body comprises a ring that is radiopaque.

9. A kit according to claim 4, wherein the length of the first, second and third catheters range from 40 to 80 cm.

10. A kit according to claim 9, wherein the inside diameter of the first external catheter ranges from 4.7 mm to 2.3 mm and from 4.0 mm to 1.67 mm for the inside diameter of the second catheter.

11. A kit according to claim 10, wherein the device that is detectable from outside the body comprises a ring that is radiopaque.

* * * * *